United States Patent
Schuppan et al.

(10) Patent No.: US 6,319,726 B1
(45) Date of Patent: Nov. 20, 2001

(54) IMMUNOLOGICAL METHOD FOR DETECTING ANTIBODIES DIRECTED AGAINST TISSUE TRANSGLUTAMINASE (TTG), USE OF TTG IN DIAGNOSIS AND THERAPY CONTROL, AND AN ORAL PHARMACEUTICAL AGENT CONTAINING TTG

(76) Inventors: Detlef Schuppan, No. 28, Markelstr.28, 12163 Berlin; Walburga Dieterich, No. 19, Kreuznacher Strasse, D-14197 Berlin; Tobias Ehnis, No. 17, Kreuznacher Strasse, D-14197 Berlin, all of (DE)

( * ) Notice: Subject to any disclaimer, the term of this patent is extended or adjusted under 35 U.S.C. 154(b) by 0 days.

(21) Appl. No.: 09/229,716

(22) Filed: Jan. 13, 1999

Related U.S. Application Data

(63) Continuation of application No. PCT/EP97/03740, filed on Jul. 14, 1997.

(30) Foreign Application Priority Data

Jul. 18, 1996 (DE) .............................. 196 30 557

(51) Int. Cl.$^7$ ................................. G01N 33/564

(52) U.S. Cl. .................. 436/506; 436/513; 436/518; 435/7.94

(58) Field of Search ................................. 436/506, 513, 436/518; 435/7.94

(56) References Cited

U.S. PATENT DOCUMENTS 5,464,615 * 11/1995 Stief et al. .......................... 424/94.63
5,716,794 * 2/1998 Tjota .................................. 435/7.92

FOREIGN PATENT DOCUMENTS 19520480  12/1996 (DE) .

OTHER PUBLICATIONS

"Autoantibodies to Gliadin–Binding 90 kda glycoprotein in coeliac disease" by Maury et al.; pp. 147–152. (Gut. 1986, 27).

"Identification of tissue transglutaminase as the autoantigen of celiac disease" by Dieterich et al.; Nature Medicine, vol. 3, No. 7, Jul. 1997; pp. 797–801.

"Revised Criteria for Diagnosis of Coeliac Disease" Archives of Disease in Childhood 1990; 65.

"IgA Antiendomysial Antibody Test—A Step Forward in Celiac Disease Screening" by Volta et al.; Digestive Diseases and Sciences, vol. 36, No. 6 (Jun. 1991) pp. 752–756.

"Predictive Value for Coeliac Disease of Antibodies to Gliadin, Endomysium, and Jejunum in Patients Attending for Jejunal Biopsy" by McMillan et al.; vol. 303, No. 9, 1991 pp. 1163–1165.

"Antigliadin and Antiendomysium Antibody Determination for Coeliac Disease" by Bürgin–Wolff et al. Archives of Disease in Childhood 1991: 66 pp. 941–947.

"Anti–Endomysial Antibodies—A Serologic Marker of Dermatitis Herpetiformis" by Accetta et al.; Arch Dermatol—vol. 122, Apr. 1988, pp. 459–462.

"IgA Antiendomysium Antibodies Have a High Positive Predictive Value for Celiac Disease in Asymptomatic Patients" by Grodzinsky et al.; Allergy 1994; 49: pp. 593–597.

"Disease Specificity and Dynamics of Changes in IgA Class Anti–Endomysial Antibodies in Celiac Disease" by Kapuscinska et al.; J. Pediatr Gastroenterol Nutr. 1987 Jul. 6(4): 529–534. Abstract.

"Endomysial Antibodies in the Diagnosis of Celiac Disease and the Effect of Gluten on Antibody Titers" by Lerner et al.; Ernest Witebsky Center for Immunology, Dept of Microbiology, SUNY. Buffalo; Immunol Invest 1989; Jan. 18(1–4): 533–544. Abstract.

"Demonstration of Tissue 90 kD Glycoprotein as Antigen in Circulating IgG Immune Complexes in Dermatitis Herpetitformis and Coeliac Disease" by Maury et al.; pp. 892–894. The Lancet, Oct. 20, 1984.

"Enzyme Immunoassay of Antibodies to Epithelial Glycoprotein: Increased Level of Antibodies in Coeliac Disease" by Teppo et al.; Journal Of Immunological Methods 74(1984) pp. 327–336.

"Colocalization of Tissue *Transglutaminase* and Stress Fibers in Human Vascular Smooth Muscle Cells and Human Umbilical Vein Endothelial Cells" by Chowdbury et al.; Exp. Cell Res. 1997, Feb. 25;231(1):38–49. Abstract.

"IgA Anti–Endomysium Antibody. A New Immunological Marker of Dermatitis Herpetiformis and Coeliac Disease" by Choizelski et al; Br.J. Dermotol 1984 Oct. 11 1(4):395–402. Abstract.

"Transglutaminase–Mediated Cross–Linking of Fibrinogen by Human Umbilical Vein Endothelial Cells" by Rich et al; J. Biol. Chem. 1989; Dec. 5:264(34): Abstract.

(List continued on next page.)

Primary Examiner—Donna C. Wortman

(57) ABSTRACT

The invention relates to a method for detecting antibodies from body fluids by means of an immune reaction with tissue transglutaminase (tTG), with tTG-containing compounds, the antigenic structures, immunoreactive sequences or analogues thereof. The method may be used in the diagnosis and therapy control of diseases associated with an immune reaction against tTG, tTG-containing compounds, the antigenic structures, immunoreactive sequences or analogues thereof. Therefore, the invention is also directed to the use of tTG and the above-mentioned substances in diagnosis and therapy control, preferably in the diagnosis and therapy control of chronically inflammatory diseases or autoimmune diseases, and more preferably, in the diagnosis and therapy control of sprue or coeliac disease.

14 Claims, 3 Drawing Sheets

OTHER PUBLICATIONS

Figure 3A:
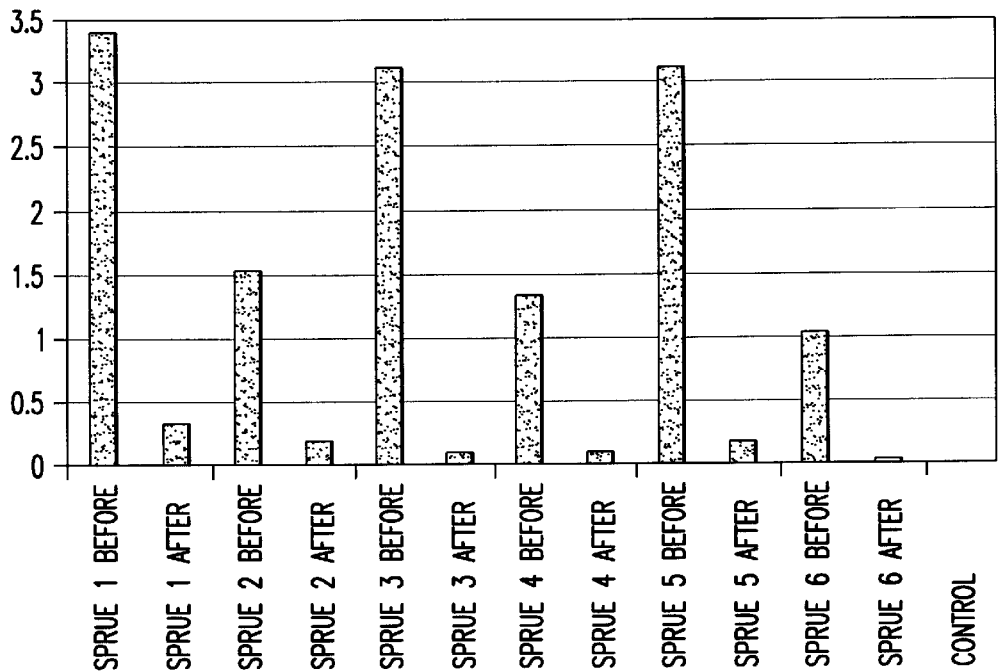

"IgA Anti–Endomysial Antibodies on Human Umbilical Cord Tissue for Celiac Disease Screening. Save both Money and Monkeys" by Volta et al.; Dig. Dir. Sci 40(9): 1902–1905 (1995).

"A Monoclonal Antibody to Cellular Transglutaminase" by Birckbichler et al.; Hybridoma; vol. 4, No. 2, 1985; Mary Ann Liebert, Inc. Publishers pp. 179–186.

"Two Antigenic Sites of Tissue Transglutaminase" by Fesus et al. Biochemistry, vol. 16, No. 18, 1977; pp. 4061–4066.

"Immunofluorescent Localization of Transglutaminase in Rat Small Intestine" by Sharp et al; Cell Biochemistry and Function; vol. 6: 137–141 (1988).

"Human Serum Transglutaminase and Coeliac Disease: Correlation Between Serum and Mucosal Activity in an Experimental Model of Rat Small Bowel Enteropathy" by D'Argenio et al.; Gut. 1989, 30, pp. 950–954.

"Purification of Fibroblast–Derived Celiac Disease Autoantigen Molecules" by Marttinen et al; Pediatric Res. vol. 34, No. 4, 1993 pp. 420–423.

"Reaction of Human Non–Collagenous Polypeptides with Coeliac Disease Autoantibodies" by Mäki et al; The Lancet vol. 338; Sep. 21, 1991 pp. 724–725.

"In Vitro Cross–Linking of Gluten into High–Molecular-Weight Polymers with Transglutaminase" by Szabolos et al; Acta Paediatrica Hungarica 28 (3–4) pp. 215–227 (1987).

"Tissue (Type II) Transglutaminase Covalently Incorporates Itself, Fibrinogen, or Fibronectin into High Molecular Weight Complexes on the Extracellular Surface of Isolated Hepatocytes" Use of 2–[(2–Oxopropyl)thio]imidazolium Derivatives as Cellular Transglutaminase Inactivators; The Journal of Biological Chemistry—vol. 266, No. 33, Issue of Nov. 25, pp. 22501–22509; 1991.

"Human Jejunal Transglutaminase: Demonstration of Activity, Enzyme Kinetics and Substrate Specificity with Special Relation to Gliadin and Coeliac Disease" by Bruce et al; Clinical Science (1985) 68, pp. 573–579.

"Isolation of Antigens Recognized by Coeliac Disease Autoantibodies and their use in Enzyme Immunoassay of Endomysium and Reticulin Antibody–Positive Human Sera" by Börner et al; Clin, Exp. Immunol 1996; 106, pp. 344–350.

"Possible Involvement of Transglutaminase in Endocytosis and Antigen Presentation" by Teshigawara et al; Microbial. Immunol. vol. 29 (8), pp. 737–750, 1985.

"Differential Expression of Tissue Transglutaminase in Human Cells—An Immunohistochemical Study" by Thomazy et al; Cell Tissue Res (1989) 255: pp. 215–224.

Dieterich et al., Sep. 17–21, 1995 (distributed at meeting), "Characterization of the autoantigens in coeliac disease", abstract presented at the 4th United European Gastroenterology Week in Berlin, Sep. 17–21, 1995, Gut supplement pp. A76–77, abstract No. 773.

Roche Lexikon Medizin, Urban & Schwarzenberg Verlag, p. 1806.

Marttinen and Mäki, 1993, "Purification of fibroblastderived celiac disease autoantigen molecules", Pediatric Res. 34(4):420–423.

Sategna–Guidetti et al., Sep. 1993, "Serum IgA antiendomysium antibody titers as a marker of intestinal involvement and diet compliance in adult celiac sprue", J. Clin. Gastroenterol. 17(2):123–127.

Barsigian et al., Nov. 1991, "Tissue (type II) transglutaminase covalently incorporates itself, fibrinogen, or fibronectin to high molecular weight complexes on the extracellular surface of isolated hepatocytes", J. Biol. Chem. 266(33):22501–22509.

Mäki et al., Sep. 1991, "Reaction of human non–collagenous polypeptides with coeliac disease autoantibodies", The Lancet, Sep. 21, 1991, pp. 724–725.

McMillan et al., Nov. 1991, "Predictive value for coeliac disease of antibodies to gliadin, endomysium and jejunum in patients attending for jejunal biopsy", BMJ 303:1163–1165.

Walker–Smith et al., 1990, Working Group of European Society of Paediatric Gastroenterology and Nutrition, "Revised criteria for diagnosis of coeliac disease", Archives of Disease in Childhood 65:909–911.

Martiner et al., Dec. 1989, "Transglutaminase–mediated cross–linking of fibrinogen by human umbilical vein endothelial cells", J. Biol. Chem. 264(34):20502–20508.

Accetta et al., Apr. 1988, "Anti–endomysial antibodies—a serologic marker of dermatitis herpetiformis", Arch, dermatol. 122:459–462.

Maury et al., 1986, "Autoantibodies to gliadin–binding 90 kd glycoprotein in coeliac disease", Gut 27:147–152.

Maury et al., Oct. 1984, "Demonstration of tissue 90 kD glycoprotein as antigen in circulating IgG immune complexes in dermatitis herpetiformis and coeliac disease", The Lancet, Oct. 20, 1984, pp. 892–894.

Product insert: "Indirect immunofluorescence test for the detection of anti–endomysial antibodies in serum with sections of human umbilical cord", for "Ab Anti–Endomysium Cord–Code 10700C" by IPR S.p.A. (Immuno Pharmacology Research).

Product insert: "Indirect immunofluorescence test for the detection of anti–endomysial antibodies in serum with sections of baboon oseophagus", for "Ab Anti–Endomysium Oseophagus–Code 10600C", by IPR S.p.A. (Immuno Pharmacology Research).

Peters and Bjarnason, 1984, "Coeliac syndrome: biochemical mechanisms and the missing peptidase hypothesis revisited", Gut 25:913–918.

Translation of Opposition Brief by Inova Diagnostics Inc. submitted on Oct. 2, 1998 to the German Patent Office.

Translation of Opposition Brief by Medipan Diagnostica GmbH submitted on Sep. 30, 1998 to the German Patent Office.

Translation of Opposition Brief by Immuno Pharmacology Research S.p.A., submitted on Oct. 2, 1998 to the German Patent Office.

Response filed in the German Patent Office on Mar. 17, 1999 by Patentees of granted German Patent Application No. DE 196 30 557.8 to the Oppositions by Inova Diagnostics Inc., Medipan Diagnostica GmbH, and Immuno Pharmacology Research.

Letter from Dr. Steven Gutman of the Food and Drug Administration to Mr. Brys Myers of INOVA Diagnostics, Inc., dated Aug. 27, 1998.

* cited by examiner

Illustration of the Autoantigen in the SDS
PAGE Following Immunoprecipitation (IP)

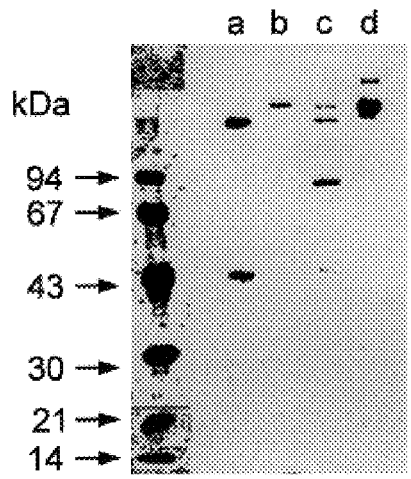

a: IP of cell lysate with control serum
b: IP of medium with control serum
c: IP of cell lysate with sprue serum, illustration of the
   auto antigen of the invention
d: IP of medium with sprue serum

FIG. 1

Protease Digestion of the Autoantigen
with Endoprotease Asp-N

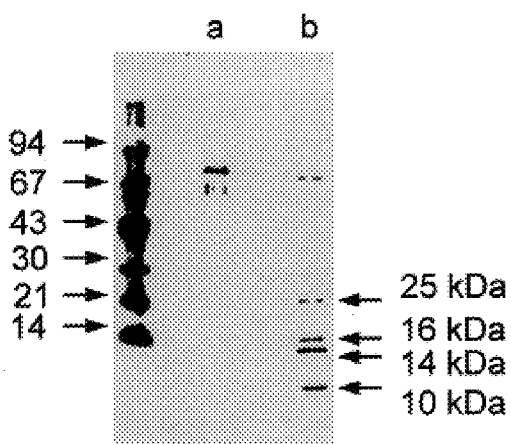

a: Autoantigen according to the invention
b: Fragments of the autoantigen after protease digestion

FIG. 2

IMMUNOLOGICAL METHOD FOR DETECTING ANTIBODIES DIRECTED AGAINST TISSUE TRANSGLUTAMINASE (TTG), USE OF TTG IN DIAGNOSIS AND THERAPY CONTROL, AND AN ORAL PHARMACEUTICAL AGENT CONTAINING TTG

This is a continuation of copending International application No. PCT/EP97/03740 filed Jul. 14, 1997.

SPECIFICATION

The invention relates to a method for detecting antibodies from body fluids by means of an immune reaction with tissue transglutaminase (tTG), the antigenic structures, immunoreactive sequences or analogues thereof, and with tTG-containing compounds, the antigenic structures, immunoreactive sequences or analogues thereof. The method may be used in the diagnosis and therapy control of diseases associated with an immune reaction against tTG, tTG-containing compounds, and antigenic structures, immunoreactive sequences or analogues thereof. Therefore, the invention is also directed to the use of tTG and the above-mentioned substances in diagnosis and therapy control, preferably in the diagnosis and therapy control of chronically inflammatory diseases or autoimmune diseases, and more preferably in the diagnosis and therapy control of sprue or coeliac disease. The invention is also directed to an oral pharmaceutical agent which includes tTG, tTG-containing compounds, the antigenic structures, immunoreactive sequences or analogues thereof as active ingredients and may be employed in the treatment of diseases accompanied by an immune reaction against these substances, because oral administration of the above-mentioned compounds results in an immune tolerance.

The present invention is based on the discovery that tissue transglutaminase (tTG, EC 2.3.2.13) is the autoantigen of sprue or coeliac disease.

On the basis of the above finding, the immunological method of the invention for detecting antibodies against tTG and tTG-containing compounds has been developed.

Coeliac disease is a disease of the small intestine mucosa, the first manifestation predominantly occurring during the late infant and toddler ages. If the corresponding clinical picture does not occur before the adult age, it is termed non-tropical sprue. Thus, both of these terms describe the same disease. Sprue is accompanied by an inflammatory change of the mucosa and a general malabsorption as a result thereof. In most of the cases, there is a morphological and clinical response to a treatment using a diet free of gluten.

Well-known as pathogenic factors are glutens from wheat, barley, rye and, to some extent, oats, while those from plant types having a lower degree of phylogenetic relation, such as corn, rice and soy are non-pathogenic. Amongst said glutens, the role of the pathogenic agent is ascribed to the alcohol-soluble prolamins, specifically α-gliadin.

For this reason, sprue preferentially occurs in countries where wheat is used as major source of food (Europe, U.S.A, Australia) and has an incidence rate of 0.14/1,000 newborns in Denmark, 0.7/1,000 in Spain, 1/1,000 in Italy, 0.45/1000 in Germany, and 2.42/1,000 in Sweden, for example.

However, more recent investigations demonstrate that a subclinical pattern, i.e., a morphological change of the mucosa without massive symptoms is more widespread than believed so far. Thus, a study carried out in Italy in 1994 revealed an incidence of 3.28/1,000 among school children.

The risk of latent sprue in the next of kin of sprue patients ranges up to 50%.

The predominantly latent sprue is frequently accompanied by a polymorphic dermatosis, i.e., *Dermatitis herpetiformis,* where characteristic subepidermal small blisters with granular IgA deposits in the dermal papillae tips can be observed. Biopsies of the small intestine show an irregular, more or less severely damaged mucosa.

Another well-established association can be observed between sprue and insulin-dependent *Diabetes mellitus,* thyroid gland diseases, and a selective IgA deficiency.

In addition to numerous concomitant clinical symptoms of sprue, such as anemia which, among other things, has been ascribed to a vitamin $B_{12}$ malabsorption, and a vitamin K deficiency representing the reason for an increased hemorrhage tendency, the massively increased risk of gastrointestinal malignant tumors plays a special role. Up to 15% of the sprue patients, mostly at an age of more than 50 years, develop neoplastic diseases, about 50% of which involving intestinal T cell lymphomas and another 25% involving esophagus, oropharyngeal and small intestine tumors.

The therapy of sprue comprises strict observance of a lifelong gluten-free diet, where not only gluten-containing products made of wheat but also those made of rye, barley and oats must be excluded. As for the patients, this represents a grave restriction in both eating habits and social interactions.

If diagnosis and therapy of sprue are effected in time, there is a good prognosis. However, complications once having occurred are frequently not completely reversible. Conversely, if the disease remains unrecognized and untreated, severe symptoms may arise as a result of malabsorption. Ultimately, there is an increased risk of developing intestinal lymphomas and other gastrointestinal neoplasias.

At present, biopsy of the small intestine represents the top level standard in the diagnosis of sprue and the follow-up under gluten-free diet, but also non-invasive diagnostic methods based on immunological markers become more and more important. Because IgA and IgG class antibodies are present in the serums of sprue patients, which, on the one hand, are directed against gliadin and, on the other hand, against an autoantigen of the endomysium which is a special connective tissue which, among other things, contains the collagens I, III and V, elastic fibers, noncollagenic proteins such as fibronectin and proteoglycans, the serums may be tested for IgG and IgA antibodies against gliadin using ELISA, and for IgG and IgA antibodies against endomysium using indirect immunofluorescence. While antibodies against gliadin are not sufficiently specific for sprue, high sensitivity and specificity (97–100%) are reported for the IgA Ab against endomysium. However, esophagus sections from primates are required for the immunofluorescence detection. At present, attempts are made to detect the endomysium antibodies on umbilical cord material as well.

With a timely diagnosis and a strict observance of a gluten-free diet, the disease may be maintained in remission and thus, the increased risk of malignant tumors of the patients can also be lowered to a normal value. Therefore, there is great interest in developing a suitable detection assay for sprue. Because the group of individuals bearing a latent sprue also belong to the high-risk group, all of the individuals in question (especially, the next of kin), and ultimately, all the school children, as is presently taken into consideration in Italy, should be examined using a sensitive, specific, easily feasible, and low-cost assay.

To date, however, large-scale screening programs failed as a result of the following problems:

The invasive duodenal biopsies of symptom-free persons are unconscionable and exceedingly expensive.

An ELISA detection based on antibodies against gliadin is scarcely useful as a result of its poor specificity.

The immunofluorescence detection of IgA class endomysium antibodies, which is based on primate esophagus, is too expensive as a general screening method. Furthermore, the assessment is subjective and does not permit identification of sprue patients having an IgA deficiency (2% of the patients).

To date, therefore, a non-invasive, specific, quantitative, rapid, easily and inexpensively feasible detection assay for sprue/coeliac disease and therapy control thereof does not exist.

This problem is solved by the present invention. Based on the surprising finding that tissue transglutaminase (tTG, EC 2.3.2.13) is the autoantigen of sprue, an immunological method according to claims 1 through 6 for detecting antibodies against tTG and tTG-containing compounds from body fluids, particularly from serum was developed, which method not only permits diagnosing sprue or coeliac disease, but all diseases accompanied by an immune reaction against tTG, tTG-containing compounds, the antigenic structures, immunoreactive sequences or analogues thereof.

The tissue transglutaminase belongs to the class of transglutaminases. The TGs (EC 2.3.2.13) are enzymes catalyzing an acyl transfer depending on $Ca^{2+}$, the γ-carboxamide groups of peptide-bonded glutamine residues acting as acyl donors. Primarily protein-bonded lysine residues function as acyl acceptors, so that the transfer results in an ε-(γ-glutamyl)lysine bond. The substrate specificity of the TGs with respect to the acyl donors is very high (depending on the amino acid sequence), whereas an exceptionally wide spectrum of acceptors is available. The covalent peptide bonds formed are highly stable and protease-resistant, resulting in an increased resistance of the crosslinked proteins to chemical, enzymatic or physical effects.

Also, the widespread occurrence of various TGs in miscellaneous organs, tissues, in plasma and interstitial body fluids correlates with the occurrence of transglutaminase-modified proteins in blood clots, on cell membranes, in the horny layer of the epidermis, in hair, nails, and in the extracellular matrix.

The described transglutaminases may be distinguished by their physical properties, their location in the body, and their primary structure.

The tissue TG (tTG) is also referred to as cellular, erythrocyte, endothelial, cytoplasmatic, liver, or type II TG, and is a monomer having a molecular weight of 75–85 kDa.

The complete amino acid sequence comprising 687 residues was derived from the cDNA. At the protein level, there is an 84% homology between the human enzyme and the enzyme from mouse macrophages and an 81% homology between the human and guinea pig enzyme. Frequently, nucleotide exchanges between these species have no effect on the amino acid sequence. The active center is highly conserved, with a marked protein homology between the three species (49 out of 51 residues being identical), and a high degree of protein homology (75%) to the a-subunit of Factor XIII.

Neither is there a signal peptide nor glycosylation, and apparently, despite multiple cysteine residues, there are no disulfide bridges. Using fluorescence hybridizations, the gene for human tissue transglutaminase was localized on chromosome 20q12. Although the mechanism of enzyme liberation still is not clear, there is unequivocal evidence that tTG with its intracellular ubiquity attains important functions within the extracellular matrix (ECM). Moreover, the $Ca^{2+}$ intracellular concentration required for tTG activity is not likely to be reached under physiological conditions, whereas sufficiently high $Ca^{2+}$ concentrations are present in the extracellular range.

Several investigations establish an association of tTG with the fibronectin ECM protein. In addition to fibronectin, the ECM molecules nidogen, the N-terminal procollagen III peptide, the collagens V and XI, osteonectin, which is a microfibril-associated glycoprotein, high molecular weight dermatan sulfate proteoglycan, and the galectin 3 lectin could be identified as specific substrates for tTG.

Indications for an important role of tTG in wound healing were also obtained from immunofluorescence studies on cultivated WI38 cells (lung embryonal fibroblasts) which do not exhibit extracellular tTG activity under normal conditions but effect extracellular deposition of the enzyme upon artificial wound generation. The possibly passive release of the enzyme from damaged cells is followed by an initially non-covalent binding to the ECM, particularly to fibronectin and fibrillary collagens, where the enzyme is catalytically active for some hours. Using a rat model, likewise after artificial wound generation, a 5 day increased tTG activity was detected. Also, when incubating human erythrocyte lysates with plasma, a strong affinity of the liberated tTG to fibronectin could be demonstrated. All the findings indicate that the tTG bound to ECM assumes a central role in the early phase of wound healing and, in particular, contributes to fibrin stabilization together with Factor XIII, forming a protective layer and a stable adhesive substrate around the damaged cells by crosslinking of extracellular proteins. To date, no enzymes capable of cleaving the tTG-catalyzed, enormously stable crosslinkages of the proteins could be detected in vertebrates.

Based on the finding that tTG is the autoantigen of sprue, the invention is also directed to the use of tTG, tTG-containing compounds, the antigenic structures, immunoreactive sequences or analogues thereof in the diagnosis and therapy control of diseases accompanied by an immune reaction against said compounds. In particular, acute inflammatory diseases such as pneumonia, glomerulonephritis, virus hepatitis, or chronically inflammatory diseases, such as Morbus Crohn, Colitis ulcerosa, or autoimmune diseases such as autoimmune hepatitis, Sjoegren syndrome, Wegener's granulomatosis, rheumatoid arthritis, idiopathic organ fibrosis, such as lung fibrosis can be diagnosed in this way. Especially suitable is the detection assay for the diagnosis and therapy control of sprue. Since this assay can be performed quickly and cost-favorably, it permits efficient screening of the population for tTG antibodies.

The tTG used according to the invention may be of animal, synthetic or recombinant origin, and the same applies for the tTG-containing compounds which, in addition, may also involve a combined origin (e.g., animal tTG in association with a synthetic peptide). In the meaning of the invention, tTG-containing compounds are understood to be chemical compounds of tTG with proteins, or analogues thereof. In the meaning of the invention, tTG analogues or analogues of these tTG-containing compounds are understood to be all those antigenic structures that undergo an immune reaction with antibodies against tTG or tTG-containing compounds, e.g., synthetic peptides. Immunoreactive sequences are understood to be fragments of tTG or tTG-containing compounds produced by proteolysis, synthesis or genetic engineering, as well as variants obtained by amino acid exchange.

The immunological detection according to the invention is performed using well-known methods. Thus, any direct (e.g., using a sensor chip) or indirect procedure may be used in the detection of patient antibodies.

In the direct procedures, binding of the antibodies to be detected to the antigen is determined through the alteration of chemical or physical properties, so that subsequent detection steps using labelled binding species are not required.

According to the invention, it is preferred to detect the tTG antibodies using an immunoassay, preferably a solid phase immunoassay, with direct or indirect coupling of a reactant to an easily detectable labelling substance. More preferably, detection may be carried out using an ELISA, an RIA, or an immunofluorescence assay. The procedures involved in such detection methods are well-known to a person skilled in the art.

In an ELISA, for example, the antigen, in the present case, e.g., tTG is bonded directly or indirectly to a carrier substance such as polystyrene. Following incubation with the antibodies to be detected, e.g., from serum of patients, the antigen-bonded antibodies are detected directly or indirectly using enzyme-coupled substances. These substances may be antibodies, fragments of antibodies, or high-affinity ligands, such as avidin which binds to a biotin label. For example, peroxidase, alkaline phosphatase, $\beta$-galactosidase, urease, or glucose oxidase are possible as enzymes. The bonded enzymes and thus, the bonded tTG antibodies, for example, may be quantified by adding a chromogenic substrate.

In a radioimmunoassay, the antigen, e.g., tTG is likewise bonded directly or indirectly to a carrier substance such as polystyrene. Following incubation with the antibodies to be detected, e.g., from serum of patients, the antigen-bonded antibodies are detected using substances bearing a radioactive label, e.g., $^{125}$I. These substances may be antibodies, fragments of antibodies, or high-affinity ligands, such as avidin which binds to a biotin label. The bonded radioactivity may be quantified using a suitable measuring instrument.

In an immunofluorescence assay, the antigen-bonded antibodies are detected according to the same principle, using substances which carry a fluorescent label, e.g., fluorescein isothiocyanate (FITC). These substances may be antibodies, fragments of antibodies, or high-affinity ligands, such as avidin which binds to a biotin label. The bonded amount of fluorescent dye is then quantified using a suitable measuring instrument.

According to the invention, it is also possible to detect the patient antibodies in an agglutination assay or a gel diffusion assay. These detection assays are also familiar to a person skilled in the art. Thus, in a gel diffusion assay, the antigen or antibody solutions, for example, are placed into closely adjoining wells of agar or agarose plates. In the present case, the antigen solution may be, e.g., the tTG solution, and the antibody solution may be blood serum, for example. As the substances diffuse out of their wells, concentration gradients are produced starting from the wells. If the overlapping antigen and antibody concentrations in the gel fall within specific ratios, and the antibody solution contains antibodies against the antigen, perceptible precipitates are formed in the gel.

In the agglutination assay, antigen (e.g., tTG)-bearing particles, e.g., from latex or polystyrene, are crosslinked by antibodies, e.g., from serum. The aggregates produced may be detected using turbidimetry, for example.

According to the invention, it is particularly preferred to perform the detection in the serum of sprue patients using an IgA-specific or IgG-specific ELISA. It was found that the tTG-based, newly developed ELISA detection of IgA antibodies in the serum of sprue patients is excellently suited for the diagnosis and therapy control of sprue as a result of its high sensitivity and specificity. This is also apparent in the follow-up of the treated patients (drop in titer during therapy). A comparison of the ELISA data of the invention with the immunofluorescence evaluations of third persons (detection of IgA anti-endomysium) shows good conformity. Incongruities especially occur with low antibody titers which, however, are a result of the indirect immunofluorescence being deemed as top level standard up to now. Inter alia, this is due to the subjective evaluation and the non-specific concurrent reactions of this prior art method.

The corresponding detection based on antibodies from other classes, exemplified by the IgG antibodies, is suitable for identifying sprue patients with IgA deficiency and for the examination of other diseases accompanied by an immune reaction against tTG.

Another improvement of this detection method results when using purified tTG from guinea pigs, human tTG, sequences or analogues obtained by proteolysis or genetic engineering, as well as synthetic immunogenic tTG peptides in the test system. An ELISA for the diagnosis and follow-up of other diseases accompanied by an immune reaction against tTG will be described in Example 3.3.

The invention is also directed to an oral pharmaceutical agent according to claim 10 for the treatment of diseases accompanied by an immune reaction against tTG, tTG-containing compounds, the antigenic structures, immunoreactive sequences or analogues thereof. Preferably, the oral administration form is a tablet or a capsule where an oral tolerance is produced by administering tTG, tTG-containing compounds, the antigenic structures, immunoreactive sequences or analogues thereof. On the one hand, said oral tolerance is achieved by oral supply of the autoantigen, and on the other hand, there is a so-called "bystander effect": if the autoantigen inducing the disease is unknown, another antigen contacting the immune system in the target organ can be used in oral therapy in some cases. This antigen then is capable of locally stimulating the antigen-specific suppressor T cells, thereby suppressing a systemic immune response. Only at higher antigen doses, an anergy of autoreactive T cells is induced.

Oral tolerance is the practical method of treating miscellaneous autoimmune diseases.

The pharmaceutical agent of the invention is preferably used in the treatment of sprue, but also for other chronic inflammatory intestinal diseases and autoimmune hepatitis.

According to the invention, tTG, tTG-containing compounds, the antigenic structures, immunoreactive sequences or analogues thereof are administered at a dosage of 0.01–100 mg/kg body weight.

The pharmaceutical agent of the invention may optionally contain pharmaceutically tolerable adjuvants, such as fillers, lubricants, disintegrants, binders, or release agents normally used in galenism. The ratio of the pharmaceutical adjuvants may vary within wide limits depending on the selected content of active ingredient, and is from 0.1 to 20% by weight in each case.

In particular, the advantages achieved with the present invention can be seen in a detection assay for sprue and the therapy control thereof, which assay is noninvasive, highly specific, and directed immediately against the agent associated with the disease. Moreover, a major advantage of the assay that has been developed is the rapid, easy and cost-favorable practicability, as well as the possibility of standardizing between different laboratories. Thereby, the assay permits efficient screening of the population for antibodies directed against tTG.

Also, as a result of the objectiveness of the assay data, the potential of quantitative evaluation is superior compared to the immunofluorescence evaluation involving subjective features. In addition, immunofluorescence evaluations, particularly with low titers, are hampered by nonspecific concurrent reactions. By using the specific autoantigen in the test system, the non--specific reactions on esophagus material of primates or on umbilical cords in immunofluorescence can be eliminated to the furthest possible extent.

Since the assay is applicable to IgA class antibodies as well as other classes of antibodies, sprue patients with IgA deficiency are also identified. The detection based on antibodies against tTG is also suitable for the identification, examination and therapy control of other diseases accompanied by an immune reaction against tTG.

Also, as a result of the identification of tTG as an autoantigen of sprue, it is possible to use same in its entity or the immunoreactive epitopes thereof (sequences, analogues or synthetic peptides produced by proteolysis or genetic engineering) in the oral therapy of sprue and other diseases accompanied by an immune response to tTG.

Embodiments

EXAMPLE 1

Isolation and Characterization of the Autoantigen 1.1. Immunofluorescence, APAAP Stainings The stainings were carried on various cell lines fixed in 100% methanol for 2 mm at −20° C.

In the immunofluorescence detection, the preparations were incubated with sprue and control serums, respectively, washed and detected using a TRITC-labelled anti-human IgA from rabbit (Schuppan et al., J. Biol. Chem. 1990; 265, 8823–32).

APAAP labelling was carried out after incubating the cells with the sprue serums, washing and subsequent detection using the APAAP complex (Cordell J. L. et al., J. Histochem. Cytochem. 1984; 32, 219–229).

Here, HT1080 (human fibrosarcoma cells) WI38 (human lung embryonal fibroblasts), Hep 1 and HepG2 (hepatocarcinoma cells) showed unequivocally positive cytoplasmatic signals with the patient serums, whereas normal serums or pretreatment with human IgA did not show any labelling. Human prepuce fibroblasts, human rhabdomyosarcoma (RD)/rat Ito/rat Morris hepatoma, and dog MDCK cells only showed from very faint to negative reactions.

1.2 Metabolic Cell Labelling and Immunoprecipitation of the Autoantigen

Characterization and isolation of the autoantigen were carried using HT1080 cells.

The cells were cultivated with L-alanyl-L-glutamine, 10% fetal calf serum (FCS, Gibco), 100 U/ml penicillin, and 100 $\mu$g/ml streptomycin (Seromed) in Dulbecco's modified Eagle medium (DMEM, Gibco) at 37° C. and 8% $CO_2$. For metabolic labelling, the cells were transferred into culture dishes of 5 cm in diameter, and once a −90% confluence was reached, they were kept in a medium free of methionine and FCS, whereafter this medium was replaced by 3 ml of an FCS-free medium containing $^{35}$S-methionine (0.2 mCi, Expre$^{35}$S$^{35}$S, NEN-Dupont). After 16–20 hours of incubation, the supernatant was removed. The cells were washed with phosphate buffer (PBS, Seromed), and subsequently lysed in 3 ml of lysis buffer (50 mM Tris-HCl, 150 mM NaCl, 0.5% Triton X-100, 0.5% IGEPAL CA-630 non-ionic detergent [Sigma], Complete® protease inhibitor [Boehringer], pH 7.5). Thereafter, an immunoprecipitation using CNBr-activated Sepharose 4B (Pharmacia) was carried out both with the medium and the cell lysate.

Activation and binding to Sepharose were conducted according to the manufacturer's instructions. After swelling and washing in 1 mM HCl, pH 2.5, the CNBr-activated Sepharose was incubated with an antibody from rabbit directed against human IgA (Dianova, 2.4 mg antibody/ml of Sepharose) in 0.1 M $NaHCO_3$, 0.5 M NaCl, pH 8.3, at 4° C. overnight. Non-bonded antibodies were removed by washing with the coupling buffer, and unoccupied binding sites were saturated by adding 1 M ethanolamine, pH 9.0, at room temperature, 2 hours. Thereafter, the Sepharose was washed 3 times alternately (10×Vol. each) with 0.1 M sodium acetate, 0.5 M NaCl, pH 4.0, and 0.1 M Tris-HCl, 0.5 M NaCl, pH 8.0, followed by incubation of the Sepharose with serums from sprue patients and healthy persons, respectively (0.5 ml serum/ml Sepharose), in coupling buffer (50 mM Tris-HCl, 150 mM NaCl, 1 mM $CaCl_2$, 1 mM $MgCl_2$, pH 8.0) at 4° C. overnight. Excess serum antibodies were removed by 3 washings with coupling buffer.

Each time, 1 ml of HT1080 medium or cell lysate (about $5 \times 10^4$ cells) of the metabolic-labelled cells was pre-incubated with 50 $\mu$l of C14B Sepharose (Pharmacia) for 30 min at room temperature, to remove non-specifically bonding proteins. Following centrifugation (10,000×g, 5 min, 4° C.), each of the supernatants were incubated with agitation at 4° C. overnight with 50 $\mu$l of the Sepharose to which IgA from the patients and control persons, respectively, had previously been bonded. The Sepharose pellets were then washed each time with 3×1 ml washing buffer (10 mM Tris-HCl, 1% IGEPAL CA-630 [Sigma], 0.5% sodium deoxycholate, 0.1% sodium lauryl sulfate, Complete® [Boehringer], pH 8.0), followed by 1 ml 10 mM Tris-HCl, pH 8.0. Then, the pellets were taken up in SDS assay buffer, incubated for 5 min at 95° C. under reducing or non-reducing conditions, separated on a 10–12.5% SDS polyacrylamide gel (Lämmli, U. K., Nature 1970; 227, 680–685), and detected using autoradiography (FIG. 1).

In further examinations, the bonded high molecular weight protein from the medium was found to be fibronectin which, inter alia, is non-specifically bonded to Sepharose.

However, a cell-associated protein of 85 kDa could be precipitated with all the 30 sprue serums used so far in this way, whereas the same was not possible with 15 control serums, including normal serums, serums from patients with Colitis ulcerosa and Sjoegren syndrome. It was concluded from this fact that this protein represents the essential autoantigen of sprue.

By means of protein staining of the gels using silver nitrate (Henkeshoven, J. et al., Electrophoresis 1985; 6, 103–112), a sharp protein band was assigned to the autoradiographically visible 85 kDa band.

1.3. Isolation and Purification of the 85 kDa Autoantigen

In order to isolate larger quantities of the autoantigen, a total of 65 culture dishes (175 cm$^2$ each) with HT1080 cells (about 10$^9$ cells) were cultivated. A short time before reaching confluence, the medium was replaced by an FCS-free medium, followed by incubation for another 16–20 hours in a $CO_2$ incubator. Lysis and immunoprecipitation, respectively, were effected as described above. The Sepharose pellet was incubated in a total of 4.5 ml SDS assay buffer with 2% DL-dithiothreitol (Sigma) for 5 min at 95° C. to detach bonded proteins and subsequently scrutinized in the analytic SDS polyacrylamide gel.

For further purification of the autoantigen, the immunoprecipitate was separated via elution electrophoresis as follows, using a Prep Cell (Model 491 BIO-RAD): 4.5 ml of the protein mixture was placed on top of a round gel (outer diameter: 3 cm) consisting of 6.5 cm separation gel (8% polyacrylamide, pH 8.8) and 1.5 cm collecting gel (4% polyacrylamide, pH 6.8) and separated by electrophoresis. The individual proteins were collected in the elution buffer (25 mM Tris-HCl, 0.1 M glycine, 0.01% SDS, pH 8.3) as fractions of 1.2 ml each (0.8 ml/min). The eluted fractions were scrutinized in the SDS PAGE, and the fractions containing the desired protein (about 15 ml) were combined and concentrated to about 1 ml overall volume using ultrafiltration (Amicon Centriprep-50, at 1,000×g).

1.4. Protease Digestion of the Autoantigen

Amongst several tested proteases, endoproteinase Asp-N (sequencing grade, Boehringer Mannheim) was determined to be suitable for fragmentation, because it permitted a largely reproducible cleavage pattern with relatively well-separable fragments. The enzyme/substrate concentration was adjusted to 1:100, and the digestion was carried out for 30 min at 37° C.

1.5. Transfer to PDVF Membrane

Following digestion of the purified autoantigen, the peptide fragments were separated on a preparative 10% Tricine gel (Schägger, H. et al., Anal Biochem. 1987; 166, 368–379) (FIG. 2) and transferred at 4° C. onto a PVDF membrane (polyvinylidene difluoride, Immobilon™, Millipore) in a semi-dry fastblot procedure using graphite-containing electrode plates (Fastblot B32/33, Biometra). To this end, the following layers were placed on the anode plate: 1.) a filter paper soaked in anode buffer 1 (300 mM Tris-HCl, 20% methanol, pH 10.4), 2.) a filter paper soaked in anode buffer 2 (30 mM Tris-HCl, 20% methanol, pH 10.4), 3.) the PVDF membrane activated in methanol and pre-equilibrated in anode buffer 2, 4.) the Tricine gel, 5.) two filter papers soaked in cathode buffer (25 mM Tris-HCl, 40 mM ε-amino-n-caproic acid, 20% methanol, pH 9.4), 6.) the cathode plate. The transfer was carried out over 35 min at 180 mA.

Thereafter, the PVDF membrane was stained in 0.1% Coomassie Blue Serva R-250, 50% methanol for 5 min, bleached with 50% methanol, 10% acetic acid, washed thoroughly with distilled water, and air-dried. The characteristic bands of the digested autoantigen at 10 kDa, 14 kDa, 16 kDa, and 25 kDa were cut out carefully and subjected to a first sequencing at the N terminus.

1.6. Edman Degradation (According to Edman and Henschen in: Needleman, S. B.: Protein Sequence Determination, Springer Verlag, Berlin. 1975; 232–279)

Sequencing using an Applied Biosystems 4778-Sequenator resulted in three amino acid sequences which were compared with the Swiss Prot 31 data base (by PC/GENES, IntelliGenetics). From these, an unequivocal assignment of the three fragments to human tissue transglutaminase (tTG, EC 2.3.2.13, protein glutamine γ-glutamyl-transferase) could be made with minimum discordance. The indications are given using the "one letter code"; X represents no identification:

| t-Transglutaminase: | 28'REKLVVRRGQPFW |
|---|---|
| 10 kDa fragment: | REKLVVRRGQPF(S) SEQ ID NO. 1 |
| t-Transglutaminase: | 581'DLYLENPEIKIRILG |
| 14 kDa fragment: | DLYLENPEIXIXILG SEQ ID NO. 2 |
| t-Transglutaminase: | 438'DITHTYKYPE |
| 16 kDa fragment: | DITLTYQYP(V) SEQ ID NO. 3 |

No equivocal sequence could be assigned to the 25 kDa fragment, because it was a peptide mixture.

EXAMPLE 2

Confirmation of Tissue Transglutaminase (tTG) as Sprue Autoantigen 2.1. Immunoprecipitation of Guinea Pig tTG Being commercially available and having sequence homology (>80%) to human tTG, the tTG from guinea pig liver (Sigma) was first separated by gel electrophoresis, in order to check the purity thereof. In addition to several other proteins, tTG, being about 50%, represents one of the major bands.

Although human tTG having 687 amino acids differs only slightly from the guinea pig protein having 690 amino acids, these two proteins show highly different migrating behavior in the SDS polyacrylamide gel. While the protein of animal origin appears at 75–80 kDa as expected, the human protein shows a distinctly less rapid migration, pretending an apparent molecular weight of 85 kDa as described in literature (Gentile, V., et al., J. Biol. Chem. 1991; 266, 478–483), despite apparently lacking N-glycosylation.

The reactivity of the human autoantibody from Sprue serums with guinea pig tTG was tested in an immunoprecipitation. To this end, 4 μg of tTG (Sigma) in 500 μl of lysis buffer and 0.5% bovine serum albumin were agitated at 4° C. overnight with sprue IgA coupled to 4B Sepharose, washed, boiled in SDS assay buffer under reducing conditions, and separated on a 10% polyacrylamide gel (cf., 4.1.2.). Here, specific precipitation of the expected band (m.w. 80 kDa) occurred, but none of the impurity.

2.2. Confirmation of tTG as Autoantigen in a Western Blot

Following separation of 2 μg of guinea pig tTG on an SDS gel and transfer onto nitrocellulose, the blot was blocked in PBS, 2% low-fat skim milk powder, 0.3% Tween 20, pH 7.3, at 4° C. overnight. This was followed by a one hour incubation with sprue serum (1/200) in the same buffer, three washing steps and a one hour incubation with alkaline phosphatase-coupled rabbit antibodies against human IgA (1/500). The blots were washed in PBS and developed with Nitro Blue Tetrazolium and 5-bromo-4-chloro-3-indolyl phosphate as substrate (Blake, M. S., et al., Anal. Biochem. 1984; 136, 175–179).

The 75–80 kDa band gave an unequivocal positive signal with the sprue serum, which is another proof that the serums of sprue patients contain IgA class antibodies against tTG, whereas control serums did not give any signal.

2.3. Confirmation of tTG as Endomysium Autoantigen Using Indirect Immunofluorescence Esophagus tissue sections from primates (Euroimmun, Germany) were used in the indirect detection of the IgA antibodies against endomysium in sprue serums and their inhibition by tTG. Following pre-incubation of 10 μl of patient serum diluted 1/320 in PBS with 0.5 or 10 μg of tTG from guinea pigs (Sigma) and 10 μg of BSA (Sigma) for 1 hour at room temperature, incubation thereof with said esophagus sections was performed for 1 hour at room temperature in humid atmosphere. Sprue serum (1/320) and serums of healthy individuals (1/50) were used as positive and negative controls, respectively. After the sections had been washed three times in PBS/0.2% BSA and air-dried, the detection of the autoantigen with a TRITC-labelled rabbit antibody against human IgA (Dianova), diluted 1/50 in PBS, was effected for 1 hour at room temperature. Excess antibodies were removed by successive washings with PBS/ 0.2% BSA, PBS, and distilled water.

The patient serum showed clear staining of the ECM by the IgA class antibodies which were inhibited by adding increasing concentrations of tTG, but not by pre-incubation with BSA. The control using serum of healthy individuals did not show any staining of the esophagus sections.

EXAMPLE 3

3.1. Development of a Sprue-Specific ELISA with IgA Antibodies for the Diagnosis and Follow-up of Sprue 1 μg of guinea pig transglutaminase (Sigma T-5398) in 100 μl PBS was pipetted into each well of polystyrene microplates (Greiner Labortechnik, 96 Wells) and incubated for 2 h at 37° C. under slightly rotating motion. Non-bonded tTG was removed by washing with PBS (3×200 μl), the free bonding sites of the wells were blocked with 1% bovine serum albumin (Sigma) in 250 μl of PBS at 4° C. overnight. After washing with PBS/0.1% Tween 20 (3×200 μl), the wells were incubated with sequential serum dilutions in PBS/0.1% Tween 20 (100 μl) for 1 hour at room temperature under slightly rotating motion, washed with PBS/0.1% Tween 20 (3×200 μl) and subsequently incubated with a peroxidase-conjugated rabbit antibody directed against human IgA (Dianova) (1/400 in 100 μl PBS/0.1% Tween 20) for 1 hour at room temperature. After washing with PBS (3 times), a 30 min incubation at room temperature in the dark, using 200 μl 0.1 M citrate buffer, 17.6 mM $H_2O_2$, 5.5 mM o-phenylenediamine hydrochloride (Sigma), pH 4.2, and subsequent detection of the formed dye in an ELISA reader (MRX, Dynatech Laboratories) at 450 nm were performed.

Figure 3B:
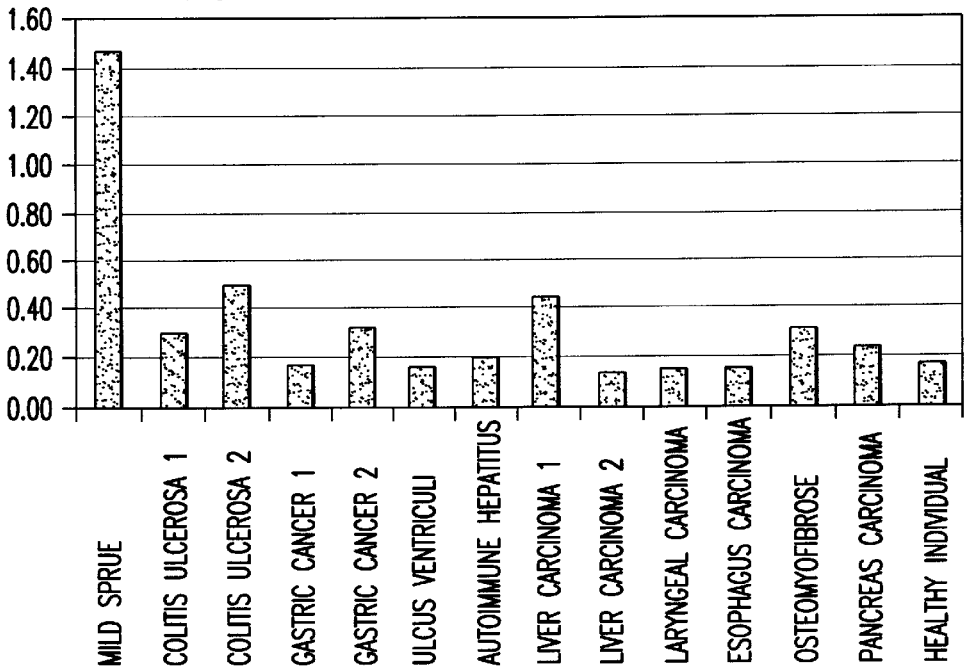

20 serums of sprue patients were tested before and after therapy using a gluten-free diet, i.e., in the active and less active phases of the disease. The test system was found to be highly sensitive, with a good correlation of the values to the sprue active phase. The therapeutical success as a result of observing a diet was reflected in a decrease of the IgA antibodies against tTG. The high specificity became obvious in the low extinction (background level) of the control serums of healthy individuals, patients with Colitis ulcerosa, liver cirrhosis, miscellaneous tumors, Sjoegren syndrome, etc. (FIG. 3).

3.2. Development of an ELISA Using Antibodies from Other Classes for the Diagnosis and Follow-up of Sprue, with IgG Antibodies as Example As about 2% of the sprue patients have an IgA deficiency, the serums were tested for their sensitivity and specificity of IgG antibodies against tTG. The ELISA was performed as in 3.1., only the peroxidase-coupled anti-human IgA antibody (Dianova) was replaced by an anti-human IgG antibody (Dianova). With respect to their sensitivity, the values of the sprue patients both before and after gluten-free diet were corresponding to the data obtained with IgA antibodies.

Figure 4:
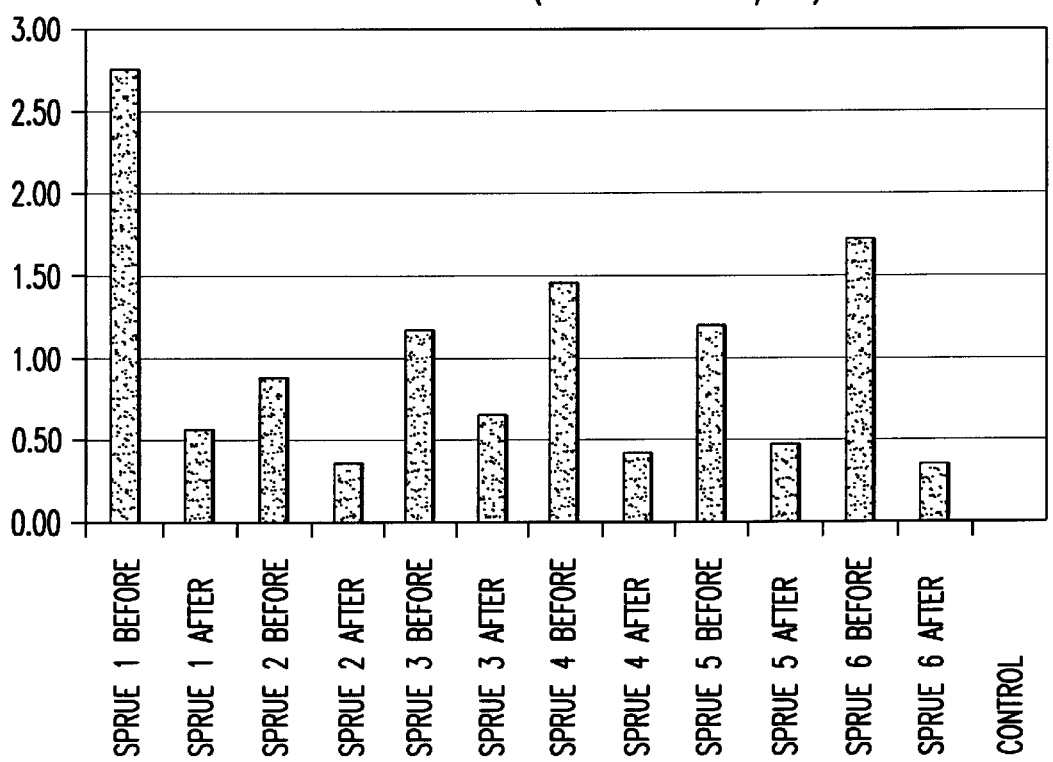

Some of the control serums showed slightly increased values, which corresponds to earlier findings of a reduced specificity of the endomysium antibodies in the indirect immunofluorescence of the IgG class (FIG. 4).

3.3. Development of an ELISA for the Diagnosis and Follow-up of Other Diseases Accompanied by an Immune Reaction against tTG, with IgG Antibodies as Example The ELISA was performed as described in 3.2.

The serums of patients with chronically inflammatory or autoimmune diseases (Colitis ulcerosa (C.U.), Morbus Crohn, acute autoimmune hepatitis) showed from slightly to moderately increased values.

Thus, by using the IgG-specific ELISA for autoantibodies against tTG, the diagnosis and therapy control of patients suffering from diseases accompanied by an immune reaction against tTG is possible.

EXAMPLE 4

A New Function of Tissue Transglutaminase (tTG) in the Crosslinking of Gliadin While a wide spectrum of acyl acceptors is available for the tTG-catalyzed reaction, only few molecules are capable of acting as acyl donors. In an in vitro experiment, the tTG-mediated incorporation of radioactively labelled putrescine into gliadin and thus, the function of gliadin as donor substrate of tTG could be established. In 160 μl of buffer (0.1 M Tris-HCl, 150 mM NaCl, 5 mM $CaCl_2$, pH 7.5), 1 μg of substrate (gliadin or control proteins such as albumin), 2 μCi [$^3$H]-putrescine, and 1 μg of tTG (from guinea pigs, Sigma) were incubated for 2 hours at 37° C. The reaction was stopped by adding 100 μl of 50% trichloroacetic acid (TCA), and the proteins were precipitated at 4° C. overnight. Following centrifugation, the pellets were washed with 10% TCA, dissolved in SDS assay buffer and, on the one hand, separated in an SDS PAGE and, on the other hand, used in a scintillation count. While no incorporation of putrescine could be determined with the controls, gliadin shows clear incorporation of [$^3$H]-putrescine both in the scintillation count data and in the SDS PAGE, proving that gliadin is an excellent substrate for tTG.

ABBREVIATIONS

Ab: Antibody
APAAP: Alkaline phosphatase anti-alkaline phosphatase
BSA: Bovine serum albumin
cm: Centimeter
DMEM: Dulbecco's modified Eagle Medium
EC: Enzyme Commission
ELISA: Enzyme-linked immunosorbent assay
ECM: Extracellular matrix
FCS: fetal calf serum
h: hour(s)
$H_2O_2$: Hydrogen peroxide
HLA: Human lymphocyte antigens
IEL: Intraepithelial lymphocytes
Ig: Immunoglobulin
kDa: Kilodalton
M: Molar
mA: Milliampere
MHC: Major histocompatibility complex
min: Minute(s)
mM: Millimolar
$M_r$: Relative molecular mass
μg: Microgram
μl: Microliter
PAGE: Polyacrylamide gel electrophoresis
PBS: Phosphate buffer
$PLA_2$: Phospholipase $A_2$
PVDF: Polyvinylidene difluoride
SDS: Sodium dodecyl sulfate
TCA: Trichloroacetic acid
TGF: Transforming growth factor
Tris: Tris(hydroxymethyl)aminomethane
tTG: Tissue transglutaminase

What is claimed is:

1. A method of identifying coeliac disease in a subject comprising the steps of:
   (i) contacting a sample of body fluid from the subject with a purified target antigen, wherein the target antigen comprises an epitope of tissue transglutaminase and has the property of being specifically recognized by at least one antibody directed towards tissue transglutaminase under conditions that allow binding of an antibody to the target antigen; and
   (ii) detecting the binding of antibodies in the body fluid to the target antigen;
wherein the binding of said antibodies bears a positive correlation with the existence of coeliac disease in the subject.

2. The method of claim 1, wherein the antibodies reactive with tissue transglutaminase in the body fluid are members of an antibody class selected from the group consisting of IgG and IgA antibodies.

3. The method of claim 1, wherein the target antigen is of human, animal, synthetic or recombinant origin.

4. The method of claim 1, wherein the target antigen is a tissue transglutaminase protein.

5. The method of claim 1, wherein the antibodies are detected by a labeled reagent that binds to the antibodies.

6. The method of claim 1, wherein the purified target antigen is bound to a solid phase reagent.

7. The method of claim 1, wherein the antibodies are detected using an assay selected from the group consisting of an ELISA, an RIA, and an immunofluorescence assay.

8. A method of identifying non-tropical sprue disease in a subject comprising the steps of:
   (i) contacting a sample of body fluid from the subject with a purified target antigen, wherein the target antigen comprises an epitope of tissue transglutaminase and has the property of being specifically recognized by at least one antibody directed towards tissue transglutaminase under conditions that allow binding of an antibody to the target antigen; and
   (ii) detecting the binding of antibodies in the body fluid to the target antigen;

wherein the binding of said antibodies bears a positive correlation with the existence of non-tropical sprue disease in the subject.

9. The method of claim 8, wherein the antibodies reactive with tissue transglutaminase in the body fluid are members of an antibody class selected from the group consisting of IgG and IgA antibodies.

10. The method of claim 8, wherein the target antigen is of human, animal, synthetic or recombinant origin.

11. The method of claim 8, wherein the target antigen is a tissue transglutaminase protein.

12. The method of claim 8, wherein the antibodies are detected by a labeled reagent that binds to the antibodies.

13. The method of claim 8, wherein the purified target antigen is bound to a solid phase reagent.

14. The method of claim 8, wherein the antibodies are detected using an assay selected from the group consisting of an ELISA, an RIA, and an immunofluorescence assay.

* * * * *

SEQUENCE LISTING

<160> NUMBER OF SEQ ID NOS: 3

<210> SEQ ID NO 1
<211> LENGTH: 26
<212> TYPE: PRT
<213> ORGANISM: Human

<400> SEQUENCE: 1

Arg Glu Lys Leu Val Val Arg Arg Gly Gln Pro Phe Trp Arg Glu Lys
1               5                   10                  15

Leu Val Val Arg Arg Gly Gln Pro Phe Ser
            20                  25

<210> SEQ ID NO 2
<211> LENGTH: 30
<212> TYPE: PRT
<213> ORGANISM: Human
<220> FEATURE:
<221> NAME/KEY: UNSURE
<222> LOCATION: (25)...(25)
<223> OTHER INFORMATION: X represents no identification.
<221> NAME/KEY: UNSURE
<222> LOCATION: (27)...(27)
<223> OTHER INFORMATION: X represents no identification.

<400> SEQUENCE: 2

Asp Leu Tyr Leu Glu Asn Pro Glu Ile Lys Ile Arg Ile Leu Gly Asp
1               5                   10                  15

Leu Tyr Leu Glu Asn Pro Glu Ile Xaa Ile Xaa Ile Leu Gly
            20                  25                  30

<210> SEQ ID NO 3
<211> LENGTH: 20
<212> TYPE: PRT
<213> ORGANISM: Human

<400> SEQUENCE: 3

Asp Ile Thr His Thr Tyr Lys Tyr Pro Glu Asp Ile Thr Leu Thr Tyr
1               5                   10                  15

Gln Tyr Pro Val
            20